(12) United States Patent
Duran

(10) Patent No.: US 8,328,417 B2
(45) Date of Patent: Dec. 11, 2012

(54) PHOTOELASTIC METHOD FOR ABSOLUTE DETERMINATION OF ZERO CTE CROSSOVER IN LOW EXPANSION SILICA-TITANIA GLASS SAMPLES

(75) Inventor: Carlos Duran, Ottawa (CA)

(73) Assignee: Corning Incorporated, Corning, NY (US)

( * ) Notice: Subject to any disclaimer, the term of this patent is extended or adjusted under 35 U.S.C. 154(b) by 359 days.

(21) Appl. No.: 12/856,728

(22) Filed: Aug. 16, 2010

(65) Prior Publication Data

US 2011/0043787 A1    Feb. 24, 2011

Related U.S. Application Data

(60) Provisional application No. 61/235,507, filed on Aug. 20, 2009.

(51) Int. Cl.
*G01L 1/24* (2006.01)
*G01N 25/16* (2006.01)
*G01N 33/38* (2006.01)

(52) U.S. Cl. ............... 374/43; 374/44; 356/33; 356/35

(58) Field of Classification Search ............ 374/43, 374/44; 356/33, 34, 35, 364, 368; 73/800
See application file for complete search history.

(56) References Cited

U.S. PATENT DOCUMENTS

| 3,745,460 | A  | * | 7/1973  | Belzer et al. ............ 324/762.05 |
| 4,192,610 | A  | * | 3/1980  | Paraskevas ...................... 356/33 |
| 5,095,515 | A  | * | 3/1992  | Seaver ........................... 385/16 |
| 5,589,931 | A  | * | 12/1996 | Rapoport et al. .............. 356/33 |
| 5,970,751 | A  |   | 10/1999 | Maxon et al. |
| 6,606,883 | B2 |   | 8/2003  | Hrdina et al. |
| 6,704,103 | B2 | * | 3/2004  | Shi et al. .................... 356/243.3 |
| 6,988,377 | B2 |   | 1/2006  | Bernas et al. |
| 7,053,017 | B2 |   | 5/2006  | Hrdina et al. |
| 7,155,936 | B2 |   | 1/2007  | Dawes et al. |
| 7,251,029 | B2 | * | 7/2007  | Kishikawa et al. .......... 356/364 |
| RE40,586  | E  |   | 11/2008 | Hrdina et al. |
| 7,506,522 | B2 |   | 3/2009  | Bleaking et al. |

FOREIGN PATENT DOCUMENTS

| JP | 62276437   | A | * | 12/1987 |
| JP | 07043326   | A | * | 2/1995  |
| JP | 2007285725 | A | * | 11/2007 |
| SU | 1185075    | A | * | 10/1985 |

* cited by examiner

*Primary Examiner* — R. A. Smith
(74) *Attorney, Agent, or Firm* — Walter M. Douglas

(57) ABSTRACT

The disclosure is directed to a photoelastic method for measuring the absolute zero crossover temperature Tzc of a sample of materials (transparent glass, glass-ceramic or ceramic) directly, without requiring calibration against a primary technique. The method involves subjecting the sample to a temperature gradient that generates a stress distribution pattern within the sample. When some portion of the sample is at a temperature equal to the Tzc of the material, the pattern adopts an easily identifiable shape whose measurement allows the calculation of Tzc. Silica-titania glass, which has a low thermal expansion, is used as an exemplary material.

18 Claims, 4 Drawing Sheets

PHOTOELASTIC METHOD FOR ABSOLUTE DETERMINATION OF ZERO CTE CROSSOVER IN LOW EXPANSION SILICA-TITANIA GLASS SAMPLES

CROSS-REFERENCE TO RELATED APPLICATIONS

This application claims the benefit of priority under 35 U.S.C. §119(e) of U.S. Provisional Application Ser. No. 61/235,507 filed on Aug. 20, 2009.

FIELD

This disclosure is directed to a photoelastic technique that can be used to directly measure the absolute zero crossover temperature ("Tzc") of glass without requiring calibration against a primary technique, and in particular to low thermal expansion glasses, for example, silica-titania glass, without requiring calibration against a primary technique.

BACKGROUND

Silica-titania glass, for example, ULE® glass (Corning Incorporated) is the material of choice for mirror substrates for use in extreme ultraviolet lithography ("EUV") tools due to its very low coefficient of thermal expansion ("CTE"). The substrates are specified within a very narrow range for the value of the average CTE zero crossover temperature ("Tzc"), which is controlled by glass composition and by the thermal history of the glass. Qualification of a glass to ensure that it fulfills specification requirements for Tzc involves measurements of CTE using an ultrasonic method. While the indirect ultrasonic method has been highly successful to date, it does have some shortcomings. For example:
1. It relies on the material having a well-defined thermal history. Measuring a material with different thermal history requires the calibration to be corrected for the specific thermal history of the material with the different thermal history.
2. There is potential for uncontrolled factors, for example, the OH content, affecting the calibration and going unnoticed, which would introduce errors in the Tzc calculated for the part.
3. Efforts to correlate the technique to absolute dilatometry show a residual error in the order of 1 to 2° C. in the crossover temperature calculated for the parts.
4. Due to its indirect nature, and its reliance on an empirical calibration, customers are uncomfortable relying on its results for qualifying material when requirements for Tzc accuracy are in the order of a few degrees C.

On the other hand, the value of Tzc can be ascertained by measuring a sample of glass in an absolute dilatometer, for example, a Fabry-Perot interferometer. While absolute dilatometry is a well established technique, it is not suitable for controlling glass in a production environment because:
1. It requires carefully finished samples, which are expensive and take a long time to manufacture (4 to 8 weeks).
2. It requires expensive specialized equipment and personnel.
3. It is potentially affected by subtle and hard to quantify effects such as the temperature dependence of reflection coatings, and the quality of optically contacted bonds.
4. Due to the relatively large size of the needed samples, it is sometimes hard to select a sample that truly represents the material used to make a part.
5. It is very slow, typically taking weeks to measure a sample.

The photoelastic sandwich seal technique can be used to measure the difference in CTE between samples of two materials using much simpler and faster equipment than is required and used for absolute dilatometry. However, there are some shortcomings to the photoelastic sandwich seal technique, for example:
1. It also requires relatively expensive and carefully made samples, with a long lead time.
2. It measures differences in CTE between two materials, and does not directly measure the absolute Tzc. Establishing absolute Tzc requires correlation to a reference technique.

For these reasons the photoelastic sandwich seal technique is not well suited for direct Tzc characterization in a production environment.

Thus, in view of the deficiencies of the known methods for measuring Tzc, there is a need for a technique that allows quick and inexpensive measurement of the absolute Tzc of a small sample of ULE® glass without the need for expensive equipment or samples that have high cost and take a long time to manufacture. In addition, such replacement method and associated equipment should be usable in production to provide an absolute reference for interferometry, which would allow this higher resolution technique to replace highly labor intensive, lower spatial resolution ultrasonic velocity measurements that are presently being used in the industry.

SUMMARY

In one embodiment this disclosure is directed to a photoelastic method as described herein that can measure the absolute Tzc of a sample of ULE® glass directly, without requiring calibration against a primary technique. The method involves subjecting the sample to a temperature gradient that generates a stress distribution pattern within the sample. When some portion of the sample is at a temperature equal to the Tzc of the material, the pattern adopts an easily identifiable shape whose measurement allows the calculation of Tzc. The method does not rely on a fixed or known composition, or on the thermal history of the glass sample, for example, ULE® glass. In addition, the method also does not depend on detailed knowledge of material parameters such as the stress-optic coefficient. The method of the present disclosure can be used to obtain a variety of technical information useful to those who make and use low expansion materials and parts. For example:
1. The method can be used as an absolute reference for calibration of secondary techniques, for example, ultrasonic velocity or interferometry.
2. The method is capable of measuring prism-shaped samples with linear dimensions of ~50 mm or less, roughly half the size required for dilatometry or ultrasonic measurements.
3. Even though the method does not measure directly the absolute CTE itself, it can provide Tzc values even more reliable than absolute dilatometry, at a fraction of the cost and complexity.
4. Although at a lower level of accuracy than the determination of Tzc, the method is sensitive to the slope of the expansivity curve, and can be used to measure said slope after elasticity correction factors are calculated.

In one embodiment the zero crossover temperature is determined with an accuracy ±1° C. In another embodiment the zero crossover temperature is determined with an accuracy ±0.5° C. In a further embodiment the zero crossover temperature is determined with an accuracy ±0.2° C.

In another embodiment this disclosure is directed to a method for determining the zero crossover temperature of a material, and in particular of a low expansion glass, having a zero crossover temperature in its expansivity curve, said method comprising:

providing a sample of a material having a selected length, width and height, and a first or top face and a second or bottom face, and a plurality of side faces, said material being transparent to light passing through the material and having a zero crossover temperature in its expansivity versus temperature curve;

providing an apparatus having a top and a bottom block of a high thermal conductivity material, elements for independently heating and/or cooling each of said blocks, a source of polarized light and a detector for measuring changes in the polarization of said light;

positioning said sample between said top and bottom blocks such that the top face of the sample is in thermal contact with the top block and bottom face is in contact with the bottom block;

independently heating or cooling the top and bottom faces to a selected temperature, wherein the selected top face temperature $T_t$ is different from the selected bottom face temperature $T_b$, and maintaining the selected temperature of the sample top and bottom faces for a time sufficient to establish a thermal gradient between the top and bottom faces;

measuring the stress distribution within the sample using a photo elastic technique consisting of measuring the changes in polarization state of a light beam traversing the sample in a direction parallel to the isothermal planes within the sample established by said thermal gradient, to determine the horizontal sample plane having the highest tensile stress;

determining the temperature profile of the sample along the vertical axis; and determining Tzc from the temperature value of the plane having the maximum tensile stress. To determine the crossover temperature, some plane in the sample must be at the crossover temperature. Hence $T_t>Tzc>T_b$, or $T_b>Tzc>T_t$. The apparatus used is placed in a chamber selected from the group consisting of a room, an environmental chamber and a vacuum chamber. The material can be a glass, glass-ceramic or ceramic, provided that the material is transparent to light passing through the material and has a zero crossover temperature in its expansivity versus temperature curve. FIG. 2 provides an example of an expansivity versus temperature curve.

DETAILED DESCRIPTION

The usefulness of the method is explained herein using ULE® glass (Corning Incorporated), which is suitable for use in EUVL applications, as an exemplary material. The method is also applicable to any material, made by any manufacturer, with a zero crossover temperature in its expansivity curve. The method can be applied to samples of material destined to be used in a wide range of applications requiring near-zero thermal expansion; for example EUVL optics, optics that are used in space mirrors, satellites optics, below 200 nm lithographic methods and other applications. The samples described herein have a length L, a width W and a height H, and the samples will have opposing top and bottom faces and a plurality of side faces such as could be found in a square, rectangular, hexagonal, octagonal, etc., shaped sample pieces. The material can be a glass, glass-ceramic or ceramic, provided that the material has a zero crossover temperature in its expansivity versus temperature curve and is transparent to light passing through it. Herein low thermal expansion glasses are those that have a CTE of <1 ppm/C.

The method disclosed herein can be carried out in a vacuum chamber, in an environmental chamber in air or other atmosphere (for example, an inert gas), or in a room, for example, a laboratory room. Herein the term "chamber" is a collective term meaning a room, an environmental chamber and a vacuum chamber unless otherwise specified. When the method is carried out in air in an environmental chamber or in air in a room, thermal leaks to the atmosphere can occur by atmospheric conduction of heat to or from the sample. Additionally, thermal currents in an open room further complicate the thermal leak problem relative to those in an environmental chamber. The method is thus "cleaner" when carried out in a vacuum chamber as thermal leaks into the environment are avoided. When a vacuum chamber is used the pressure less than $10^{-3}$ mm Hg. In one embodiment the pressure is less than $10^{-4}$ mm Hg. However, for the testing of production samples, performing the method in an environmental chamber or open room may be sufficient production purposes, and thus the setup and practice of the method disclosed herein becomes simpler and less expensive.

Figure 4:
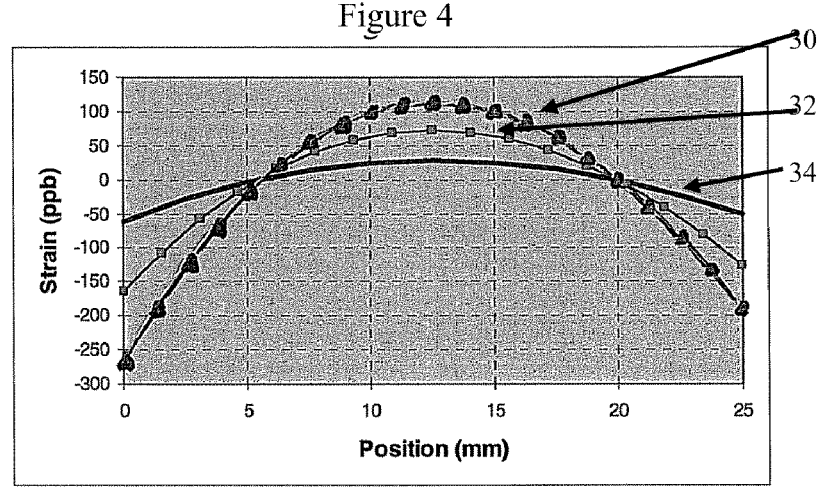
FIG. 4 is a graph illustrating horizontal strain as a function of height in a substantially homogeneous sample of ULE® glass characterized by the expansivity curve of FIG. 2 and subjected to a temperature gradient as shown in FIG. 3. Different curves correspond to varying intensities of the temperature gradient.
Figure 5:
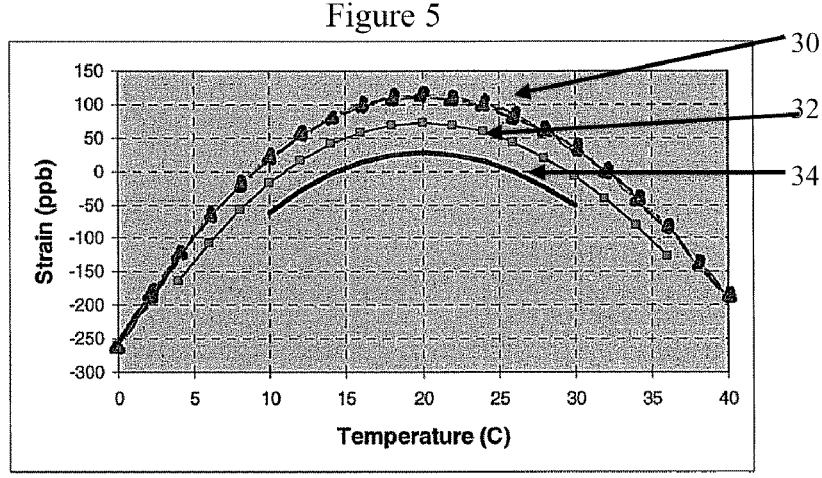
FIG. 5 is a graph illustrating horizontal strain as a function of temperature, the data being extracted from the curves of FIG. 4.

Herein in FIGS. 4 and 5, numerals 30, 32 and 34 represent a ΔT=40° C., 32° C. and 20° C., respectively. Also herein, in FIGS. 6 and 7 the numerals 40, 42 and 44 represent a Temperature at the center of the sample=18° C., 20° C. and 22° C., respectively (ΔT=20° C. in all cases).

The semiconductor industry produces the silicon chips that have fueled the Information Revolution taking place during the late 20$^{th}$ and early 21$^{st}$ centuries. The industry has succeeded in this enterprise by continuously improving the performance of semiconductor chips while simultaneously reducing their manufacturing cost. This has been achieved by means of ever increasing the optical resolution of the cornerstone piece of equipment in the semiconductor lab, the lithography scanner, which has enabled production of chips with ever shrinking feature sizes. The push for resolution has resulted in the reduction of the operating wavelength of the scanners, which has reached the limit practically attainable using traditional, refractive optics at the current wavelength of ~193 nm, generated by ArF excimer lasers. ArF scanners are presently about to reach the smallest feature sizes that they are capable of, meaning that the industry needs to find a new technology if it is to continue to increase the density of components within integrated circuits. The most likely candidate to replace lithography when this technique reaches the limit of its technical capability is extreme ultraviolet lithography (EUVL). Several pilot-line EUVL tools are currently in operation, and it is expected that chip production using this technology will start in a few years. Production-capable EUVL tools are in the design stage at this point in time. One key difference between current, pilot-line tools, and production tools, is the much higher light source intensity required by the latter in order to fulfill production throughput requirements.

EUVL is similar to current optical lithography in that it relies on an optical projection system to reproduce features from a master reticle (also known as mask) onto a thin photosensitive layer (resist) deposited on the surface of a semiconductor wafer. EUVL operates at a wavelength of ~13.4 nm, at which no known material is transparent. Thus, the EUVL projection system needs to be built based on reflective components (mirrors) rather than refractive elements (lenses). The extremely short wavelength of the radiation poses a number of challenges to the EUVL system designers; for example, reflective coatings on the mirrors are fundamentally limited to ~70% efficiency, implying that 30% of the radiation is lost at each surface. This radiation is absorbed as heat by the mirror substrate, which causes mirror deformation if the material expands or contracts with temperature changes. Additionally, since all gases absorb 13.4 nm radiation, the system must operate in vacuum, making it more difficult to remove heat from the mirrors and exacerbating the problem of mirror heating. Thus, extremely tight requirements are placed on the materials used to make the mirror substrates to be used in a EUVL system. Currently, Ultra Low Expansion (ULE®) glass, code 7973, made by Corning is a material of choice for production of EUVL projection mirrors. ULE® glass code 7973 has an extremely low Coefficient of Thermal Expansion (CTE) at room temperature, which is critical in allowing the shape of the mirror to stay constant upon heating. The material also possesses other key properties, such as low striae (which enables the production of very precise mirror surfaces), long term chemical and dimensional stability, and compatibility with a vacuum environment. Other low expansion glasses include silica, fused silica, HPFS® (Corning Incorporated), and doped silica or doped fused silica (exemplary dopants include, without limitation, fluorine, titania, germania, chlorine, hydrogen, and other dopants that render the glass opaque).

Figure 1:
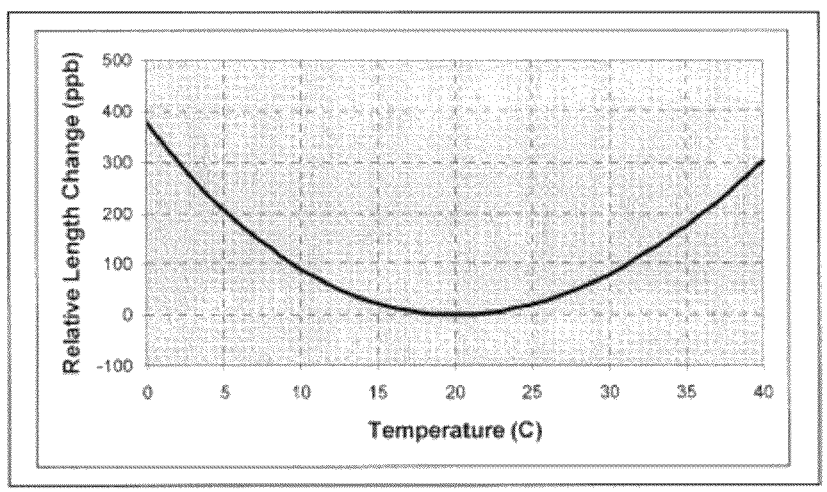
FIG. 1 is a graph illustrating the temperature dependence of the relative length of a representative piece of commercially available ULE® glass of nominal composition.

All materials either expand or contract upon changes in temperature. ULE® glass is characterized by extremely small changes in dimensions at temperatures close to room temperature, as seen in FIG. 1. As seen in FIG. 1, as the temperature increases from 0° C. to 20° C. the glass shrinks at a rate that decreases with increasing temperature; that is the relative length change decreases as the temperature increases. At 20° C. the length of the part reaches a minimum (zero relative length change in FIG. 1) and at temperature above 20° C. the length of the part increases with increasing temperature, that is, at temperatures above 20° C. the relative length change increases as the temperature increases. More specifically, the expansivity $\alpha(T)$ of ULE® glass is zero at a temperature called the "Zero Crossover Temperature" which is denoted as "Tzc" which is 20° C. in FIG. 1.

Figure 2:
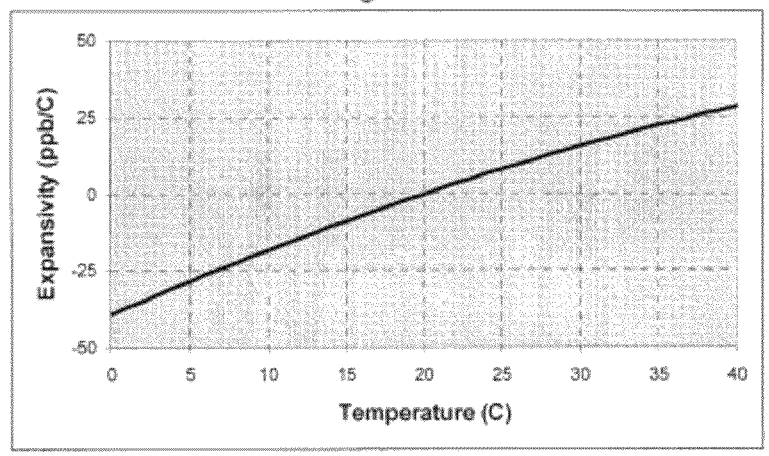
FIG. 2 is a graph illustrating the rate of change of the relative length (expansivity) versus temperature of the same glass piece of FIG. 1.

FIG. 2 illustrates the rate of change of the relative length (that is, the expansivity, $\alpha(T)$) of the same glass piece as used for FIG. 1. Below Tzc the expansivity $\alpha(T)$ is negative, and above Tzc it is positive. Based on calculations of its thermal load, size, and heat removal rates afforded by the system, EUVL system designers calculate an optimum Tzc value for each mirror in the system. This is a critical material parameter, and one that is tightly specified by the optical system designers.

Glass makers face difficulties not only in making glass that will satisfy the tight Tzc requirements, but also in measuring Tzc with the required precision. While the current ultrasonic method has proven useful, some users require additional glass samples made from material that correlates to the material used in the part. For example, these samples can be measured using Fabry-Perot interferometry, but results become available only months after the part has shipped. Results from the ultrasonic technique correlate to Fabry-Perot data with a typical error of between 1 and 2° C., which in some cases may be in the order of the specification range for Tzc. The discrepancies can arise from several factors, including material selection, sample size limitations in each of the techniques, and uncontrolled factors that may affect the empirical calibration used in the ultrasonic technique. These discrepancies are difficult to quantify and hard to eliminate. Consequently, it is highly desirable to have a new method that can be used to rapidly and accurately measure Tzc.

The present disclosure describes a photoelastic method that can be used to directly measure the absolute zero crossover temperature ("Tzc") of silica-titania glass without requiring calibration against a primary method. To exemplify the method of this disclosure, herein ULE® glass (Corning Incorporated, Corning, N.Y.) is used without limitation as an exemplary silica-titania glass. The method of this disclosure can also be used with other materials that have a zero crossover temperature in their expansivity curve, and can be applied to samples of materials destined to be used in a wide range of applications requiring near-zero expansion. For example, the method of this disclosure can be used with low temperature glasses, glass-ceramics and ceramics provided that a sample of the glass, glass-ceramic or ceramic is transparent and can be subjected to a temperature gradient that generates a stress distribution pattern within the sample. The material must be transparent because polarized light passes through the material in order to measure the stress pattern. As is described in more detail herein, when some portion of the sample is at a temperature equal to the Tzc of the material, the stress pattern adopts an easily identifiable shape whose measurement allows the calculation of Tzc. Using the method described herein, Tzc in one embodiment can be determined within ±1° C. In another embodiment Tzc is determined within ±0.5° C. In another embodiment Tzc is determined within ±0.2° C.

The method described herein involves subjecting the sample to a temperature gradient that generates a stress distribution pattern within the sample. When some portion of the sample is at a temperature equal to the Tzc of the material, the pattern adopts an easily identifiable shape, whose measurement allows the calculation of Tzc. The method does not rely on a fixed or known composition, or on the thermal history of the ULE® or other low expansion glass or other sample material. It also does not depend on detailed knowledge of material parameters such as the stress-optic coefficient. The method can be used as an absolute reference for calibration of a secondary technique, for example, ultrasonic velocity or interferometry. The method can also be used to control a final annealing step of finished parts, thus allowing extremely fine tuning of Tzc in the finished parts.

The method is capable of measuring samples in the shape of a parallelepiped, a right square prism, rectangular prism or a similar geometric form with linear dimensions of ~50 mm or less, which is roughly half the sample size required for dilatometry or ultrasonic measurements. Even though the technique does not measure directly the absolute CTE itself, the results herein indicate that it can provide Tzc values that, as a result of the data presented herein, are believed to be more reliable than absolute dilatometry, and this is accomplished at a fraction of the cost and complexity of the dilatometry method. The photoelastic method is sensitive to the slope of the expansivity curve, and can be used to measure this slope after elasticity correction factors have been calculated. Since the measurement of the slope involves this "correction factor", it is expected that the measurement of the slope of the expansivity curve will be less accurate than the measurement of the Tzc. To exemplify the utility of the photoelastic method, it is explained herein in regards to its application to ULE® silica-titania glass for use in EUVL applications, but it is not limited to either ULE® glass or a glass for EUVL applications. The photoelastic method is applicable to any material with a zero crossover temperature in its expansivity curve. It can be applied to samples of material destined to be used in a wide range of applications requiring near-zero thermal expansion, for example without limitation, astronomical mirrors (terrestrial or space), lithographic elements and masks, and satellite optics.

The zero CTE crossover temperature, Tzc, of a part made of titania-doped silica, Ultra Low Expansion ULE® glass depends on its composition and thermal history. Currently, the Tzc of ULE® parts is certified using an indirect ultrasound velocity technique, since a fast and direct method is not available. The method of the present disclosure can be used to quickly measure Tzc on small samples of ULE® glass chosen to represent a commercial part. ULE® glass is made in the form of large boules of 1-2 meters diameter and 35-60 thickness by methods described in U.S. Pat. Nos. 5,970,751, 6,606,883, 6,988,377, 7,053,017, RE40,586, 7,155,936 7,506,522. After the boules have been formed and annealed, blanks for making parts are obtained by cutting or sawing the boule into smaller pieces which are then finished to form the desired part. Optionally, the blanks can be further annealed before they are formed into parts. The samples can be extracted as of the boule material after any necessary thermal treatments, for example, annealing, are performed on the boule. As long as the sample accompanies the main parts (which are intended for EUVL use) during any heat treatments, measured changes of Tzc of the sample will reflect changes of Tzc in the main parts. This operation can be carried out more than once, if additional thermal treatments are necessary.

The method of this disclosure uses samples that are small, easy and inexpensive to manufacture (for example, a parallelepiped measuring 50 mm (L)×50 mm (W)×25 mm (H), or 2"×2"×1", where L, W and H are the length, width and height of the sample, respectively). This is a substantial advantage when compared to any other technique capable of determining Tzc at comparable levels of precision and accuracy. Since the photoelastic method is simple, fast, and economic, it lends itself to routine use in the glass manufacturing plant.

The following paragraphs further describe the method.

The method described herein is a photoelastic technique that can measure the Tzc of a sample of ULE® glass. The technique preferably involves a sample of essentially stress-free, homogenous glass in the form of a rectangular prism, with polished surfaces of good quality, but not requiring optical wringing. Optical wringing (or optical contacting) is the technique used for assembling the sandwich seals used with the photoelastic sandwich seal technique and also for attaching the mirror caps to the ends of the sample measured using the Fabry-Perot dilatometer: the surfaces are polished to very high flatness, carefully cleaned, and brought into intimate contact so that van der Walls' forces will hold the pieces together. It can produce high quality joints that will not slip under stress without the need for a bonding agent, but it requires high quality surfaces and a skilled technician, making it expensive (in particular for relatively large surfaces such as in the case of sandwich seals).

Figure 3:
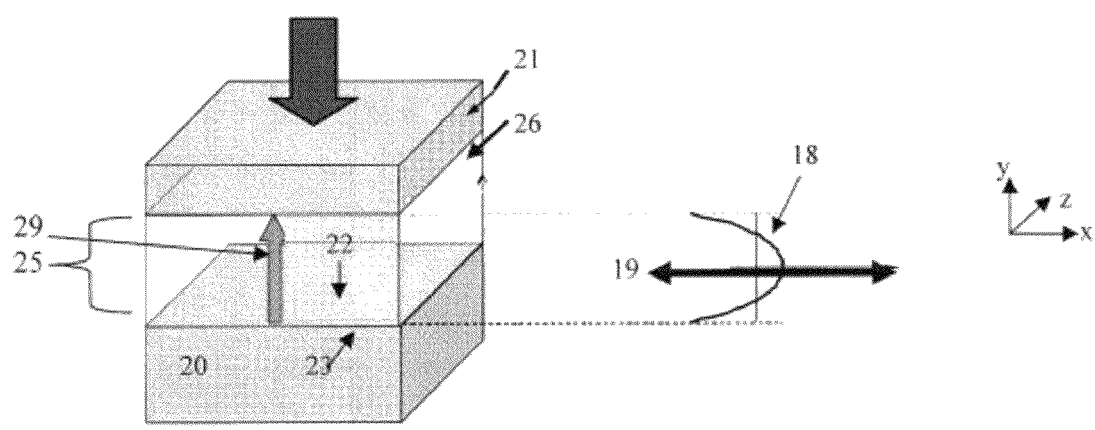
FIG. 3 is a schematic diagram illustrating the use of high thermal conductivity blocks for generating a vertical temperature gradient through same glass piece of FIGS. 1 and 2, and further illustrating the associated stress profile.

Referring to FIG. 3 (axial directions x, y and z indicated in right side diagram), a sample 25 having a first or top face and a second or bottom face is inserted into an apparatus in an environmental (e.g., glove box) or vacuum chamber (not illustrated) that allows control of the temperature around the sample, and the sample is placed on a block 20 (the "bottom block") within the chamber, the bottom block 20 being made from a material having a high thermal conductivity. A vacuum chamber is preferred. Good thermal contact between the bottom block 20 top 23 and the bottom face 22 (indicated by downward arrow) of sample 25 is required to ensure that bottom face 22 of the sample acquires a uniform temperature. The bottom block 20 top 23 does not touch the sample 25 anywhere else other than the sample 25 bottom face 22 as is shown in FIG. 3. Bottom block 20 contains heating and/or cooling elements (not illustrated in FIG. 3, see FIG. 8) for maintaining the temperature of bottom block 20 at a predetermined temperature $T_b$. The high thermal conductivity bottom block 20 has a thermal conductivity greater than 1 W/(cm K), and preferably in the range of 2 W/(cm K) to 4 W/(cm K).

The top face 26 of the sample 25 is also in contact to a block 21 of material of high thermal conductivity material (the "top block") that ensures a uniform temperature of the sample 25 top face 26. The top block 21 is intimately in contact with sample 25 top face 26 and contains embedded heating and/or cooling elements (not illustrated) for example, an electrical heater or thermoelectric element that allows controlled heating and/or cooling of top block 21 and thereby allows for heating/cooling of sample 25 by contact of top block 21 with sample 25 top face 26. Arrow 12 shows the direction of heat supplied to top block 21 for transfer to the top face 26 of sample 25. Alternatively, other arrangements are possible that enable independent and accurate control of the temperatures of the top 26 and bottom 22 faces of the sample 25, such as placing thermoelectric elements in contact with those surfaces, either directly or through temperature homogenizing elements. There is no heat flow through the lateral faces of the sample. Heat flow is in the vertical direction between blocks.

This is best achieved by performing the experiment in high vacuum (pressure less than $10^{-3}$ mm Hg, preferably less than $10^{-4}$ mm Hg), and is preferably aided by the use of an optional radiation shield. In this situation, and due to the lack of any other path for heat transfer, any heat supplied to the top block will dissipate by vertically traversing the sample. The high thermal conductivity top block 21 has a thermal conductivity greater than 1 W/(cm ° K), and preferably in the range of 2 W/(cm ° K), to 4 W/(cm ° K).

By controlling the temperature of the sample 25 bottom face 22 at a predetermined value $T_b$, and applying a constant power W to the top block 21, the top face 26 of the sample 25 acquires a temperature $T_t$, and a controlled temperature gradient is established along the vertical direction of the sample as indicated by the upward arrow 29. This gradient is equal to the difference between the temperatures at the top and the bottom of sample 25, $T_t$-$T_b$, divided by the vertical height H of the sample 25. Since the lateral faces of the sample 25 are adiabatic, the temperature distribution within the sample 25 changes in a substantially linear fashion along the vertical direction of arrow 29, and the temperature is constant within planes perpendicular to it. The temperatures $T_b$ and $T_t$ are chosen such that a plane within the sample 25 acquires a temperature equal to the Tzc of the glass that constitutes the sample. Since Tzc is generally known beforehand within a few degrees, and the difference $T_t$-$T_b$ is a few tens of degrees, this situation is easy to accomplish in practice.

If the sample is short, that is, its height "H" is smaller relative to the lateral dimensions L and W, the sample acquires an average lateral expansion given by the thermal expansion dL(T)/L integrated along the vertical direction (arrow 29). For the case of a constant vertical gradient, the average integrated expansion reduces to:

$$\langle dL \rangle / L = \int_b^t \frac{dL(T)}{L} dT$$

where L is the sample length, T is the temperature (variable along the vertical direction, $T_b$ is the temperature at the bottom face 22 of the sample and $T_t$ is the temperature at the top face 26 of the sample. Due to the temperature variation along the vertical direction (FIG. 3, arrow 29), different planes within the sample experience different amounts of strain. The strain is a function of the "y" or vertical axis only (arrow 29), and it is given by the difference between the average expansion of the whole sample, and the local expansion dL(T(y))/L, where T(y) is the local temperature associated with the plane at a height y above bottom face 22. The sample effectively behaves as a sandwich seal composed of many very thin layers, each layer having its own expansion characteristics.

The strain variation has an associated stress distribution (FIG. 3, stress profile represented by curve 18 between unnumbered dashed lines). The region of the sample at temperatures close to Tzc develops a horizontal tensile stress, while the areas away from it develop horizontal compressive stress (FIG. 3, double arrow 19). If Tzc is close enough to the center of the sample, the point with highest tensile stress corresponds to the plane of the sample that has acquired a temperature equal to Tzc. Assuming that the sample is short and if α(T) is linear with temperature, the stress depends quadratically with the vertical axis. For non-linear temperature dependence of α(T) or other sample aspect ratios, the functional dependence is more complex, but the maximum tensile stress is still observed at or very near the location of the plane at temperature equal to Tzc.

FIG. 4 shows calculated strain distributions using the actual temperature dependence of α(T) in commercial ULE® glass, for a sample measuring 25 mm in height, and assuming that the two other dimensions are much larger than the height (corrections due to finite aspect ratio of the sample are small, and they do not substantially affect the shape of the stress distribution). Different curves in FIG. 4 correspond to scenarios involving different values in the temperature difference between the top and the bottom of the sample, with all temperature distributions centered around a value of Tzc=20 C. For curve 34, ΔT=20° C., for curve 32, ΔT=32° C., and for curve 30, ΔT=40° C. The intensity of the strain increases quadratically with the amplitude of the temperature difference $T_t$-$T_b$ if α(T) is linear with temperature. The departure from this dependence is slight for the case of the actual temperature dependence of α(T) in commercial ULE® glass. FIG. 4 thus illustrates the horizontal strain as a function of height in a substantially homogeneous sample of ULE glass characterized by the expansivity curve illustrated in FIG. 2 and subjected to a temperature gradient as illustrated in FIG. 3. Positive strain is tensile while negative strain is compressive. The different curves correspond to different temperature differences between the top and bottom of the sample as described above.

Figure 8:
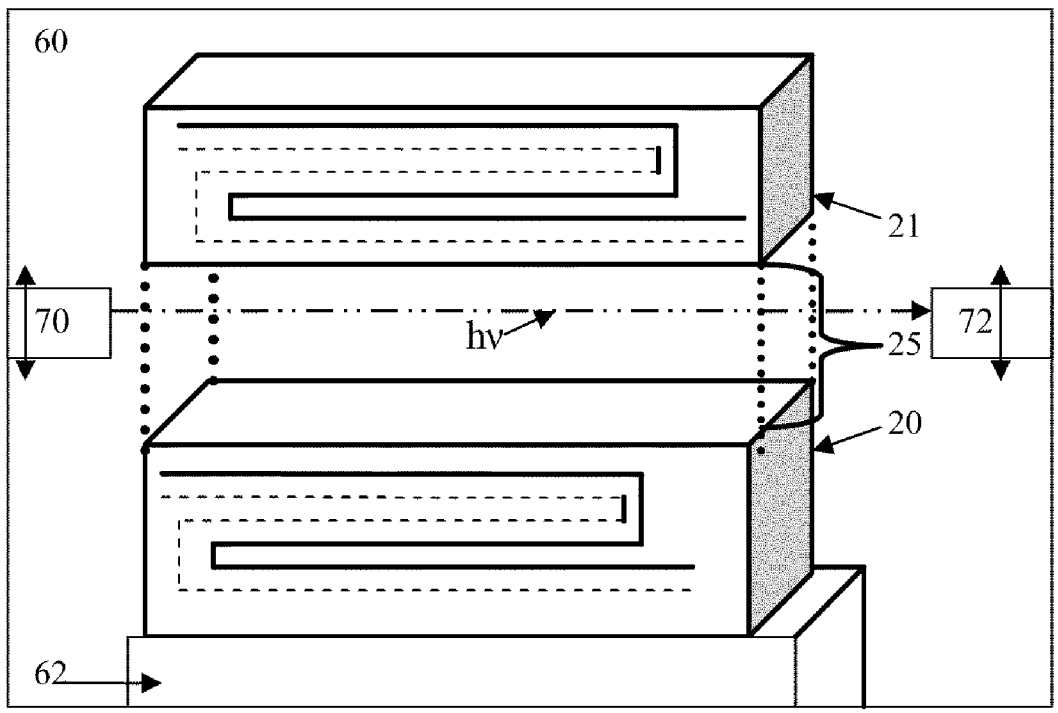
FIG. 8 is an illustration an embodiment using high thermal conductivity blocks having integrated heating and cooling elements for generating a vertical temperature gradient through a low thermal expansion glass, and further to the positions of the blocks and glass sample relative to one another within a vacuum chamber.

The stress distribution within the sample can be appropriately measured by means of a photoelastic technique, i.e., by measuring the changes in polarization state of a light beam traversing the sample in a direction parallel to the isothermal planes (see FIG. 8). There are no constrains on the wavelength of the light beam, other than transparency of the sample at the working wavelength. Availability of off-the-shelf optical components and convenience make it practical to work within the visible range. The stress profile is fitted with an appropriate functional form and the geometrical position of the maximum tensile stress is determined. The temperature distribution within the sample can be calculated by solving the heat diffusion equation. Due to the one-dimensional nature of the heat flow problem, and the fact that the thermal conductivity of glass is nearly constant for a relatively narrow range around room temperature, the temperature variation along the vertical axis is linear with height to a very good degree of approximation. Thus, the geometrical position of the measured maximum tensile stress can be uniquely associated to a temperature, which represents the measured value of the crossover temperature Tzc.

The stress measured by means of a photoelastic technique is substantially proportional to the strain curves in FIGS. 4 and 5, with a correction due to the dependence of the elastic constants and the stress-optic coefficient of the glass with temperature. This correction is small (even negligible) and can be easily calculated and fully accounted for at the time of the measurement. FIG. 5 shows strain as a function of the local temperature for the same three scenarios in FIG. 4, obtained using the linear dependence of temperature with vertical position, which has been extracted from the curves in FIG. 4 and the fixed values of T at the bottom and top surfaces of sample 25. The measurement of Tzc relies purely on the position of the maximum tensile strain in the sample, not on the intensity of the strain itself. Thus, the measurement of Tzc is not subject to measurement errors stemming from imperfect knowledge of factors such as the stress-optic coefficient or sample finite size elastic corrections.

Figure 6:
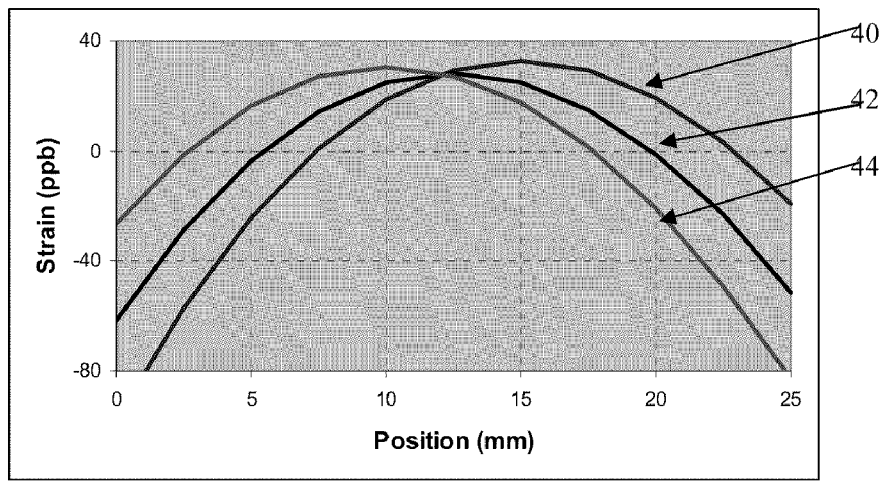
FIG. 6 is a graph illustrating horizontal strain as a function of temperature for different values of the temperature at the center of the sample.
Figure 7:
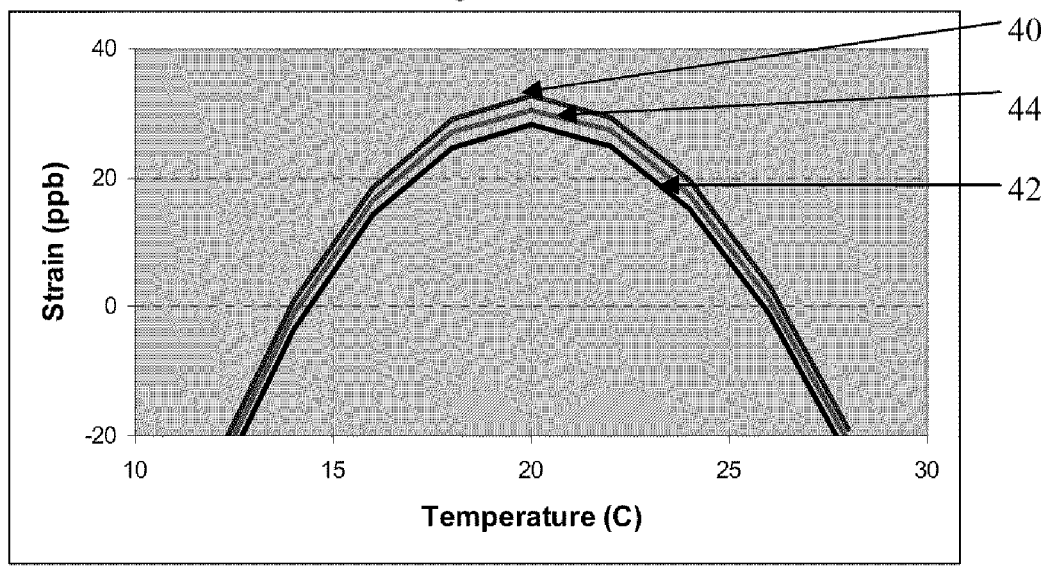
FIG. 7 is a graph illustrating horizontal strain as a function of temperature extracted using the curves of FIG. 6.

The measurement can be preferably repeated for several different values of $T_b$ and/or $T_t$, enabling a more accurate measurement of Tzc, and the calculation of corrections due to nonlinearities, and specifically the non-symmetric nature of the variations of α(T) around Tzc in ULE® glass, and any other effects that result in maximum tensile stress of the geometrical center of the sample can easily be determined. These effects are rather small, and quite often negligible, as evidenced by the curves in FIGS. 6 and 7, which show the effect on strain distributions of temperature scenarios where Tzc is not half way between $T_b$ and $T_t$. In FIG. 6 horizontal strain was determined as a function of position for different values of the temperature at the center of the sample (center temperature=$T_c$). Curves 40, 42 and 44 represent $T_c$ values of 18, 20 and 22° C., respectively, and ΔT in all cases is 20° C. FIG. 7, in which curves 40, 42 and 44 have the same meaning as in FIG. 6, illustrates horizontal strain as a function of temperature and was extracted from the curves of FIG. 6. FIG. 7 illustrates that although the intensity of the tensile strain changes with $T_c$, the maximum tensile strain is still observed at Tzc for values of $T_c$ within a few degrees of Tzc (at least 2 degrees and probably up to 4 degrees).

Effects due to non-homogeneity of the sample are not always negligible. In particular, a sample whose Tzc varies along the vertical axis (as shown in FIG. 3), will present strain distributions significantly different from the ones shown in FIGS. 4 through 7. This situation can be avoided by carefully selecting the sample, for example without limitation, by using the known rotational symmetry of the boule of the glass. In addition, the effect can be exactly cancelled by performing pairs of measurements with reverse temperature gradients, that is, by reversing the temperatures $T_b$ and $T_t$ in the experiments.

Non-homogeneity of the sample along the other two axes has no detrimental effect on the measurements on ULE® glass. This is due to the fact that variations of Tzc in ULE® are associated purely with a shift parallel to the y axis of the expansivity curve in FIG. 2. It is also notable that the photoelastic method described herein does not rely on any empirical calibration parameters. For example, the stress-optic coefficient of the material, K, enters the measured stress curve as a multiplier to its amplitude, but does not affect the shape of the measured stress distribution. Likewise, stress reductions due to sample shape elastic effects affect the measured stress magnitudes, but only affect the spatial dependence at a higher order. These effects can be accounted for and corrected by means of measurements in which the vertical position of the maximum tensile stress is varied around the center of the sample.

The magnitude of the stress distribution depends quadratically on the magnitude of the temperature gradient along the sample (FIGS. 4 through 7), and linearly on the slope of the expansivity with temperature. The typical value for ULE® glass is between 1.0 and 3.0 ppb/$K^2$; even at this small value, measurable stress profiles can be generated using temperature differences of 20 to 40° C. between the bottom and the top of the sample. This measurement temperature range is in line with typical values for establishing mean CTE in standard practices and is narrow compared to nonlinearities in the temperature dependence of the expansivity. The measurement temperature range is also narrow enough with respect to variations in the thermal conductivity of the glass. Materials with a smaller α(T) slope potentially require larger gradients, but nonlinearities are also smaller.

The required sample sizes are compatible with volumes of homogeneous properties in typical ULE® glass production, and are similar or smaller to other samples made for glass characterization. Specifically, appropriate samples can be made from within samples currently made for ultrasonic CTE measurements. For these sizes, the required temperature gradients can be easily generated with moderate power W supplied to or removed from the bottom and top block (generally in tens of Watts).

The photo elastic method described herein possesses self diagnostic characteristics. Since the method involves fitting the observed stress profiles to a known function, potential problems stemming from sample non-homogeneity can be detected. The use of a multiplicity of temperature gradients serves the function of cross-verification in addition to better definition of the measured Tzc.

In order to facilitate the task of selecting material with sufficiently uniform CTE, and the establishment of a uniform temperature gradient along the sample, smaller samples are desirable and the method enables the use of small samples of ULE® glass. Smaller sample volume requirements also add flexibility in terms of extraction of suitable samples for the purpose of qualifying sellable parts, and make the experimental setup smaller and more economical.

In one embodiment the disclosure is directed to the use of top and bottom blocks made of the same or similar material and dimensions, each attached to a thermoelectric cooler ("TEC") element, and containing optional additional heaters for temperature control. If the system is built in a symmetrical fashion, varying the direction of the currents circulating through the TECs allows changing the sign of the temperature gradient; as discussed above, combining measurements carried out using gradients of opposite signs allows the elimination of some errors arising from non-homogeneity of the glass sample. An additional advantage of the use of TECs is that measurements can be carried out at temperatures at or below room temperature without the use of cryogens. This is desirable in a plant environment in general, and it also allows fuller automation of production measurement routines.

FIG. 8 illustrates an embodiment in which the heating and cooling elements are integrated into the top and bottom blocks. In FIG. 8 the heating and cooling elements are integrated into the top 21 and bottom 20 blocks, the heating element(s) being represented by the solid line and the cooling element(s) being represented by the dashed line. The sample 25 is positioned between blocks 20 and 21 as is also illustrated in FIG. 3. The blocks 20 and 21 are within an environmental or vacuum chamber 60 (entry and exit ports, ports for connections to the heating and cooling elements, vacuum ports and other items associated with the environmental or vacuum chamber are not illustrates for simplicity) and the bottom block 20 rests on a support 62 that is made of a low thermal conductivity material. A vacuum chamber is preferred. Sample 25 surfaces can be heated or cooled by separate control of the heating/cooling elements within the blocks to thereby generate a thermal gradient through the sample. Heating elements can be most conveniently realized through electrical resistors, and both heating and cooling can be accomplished by circulating liquids through serpentine conduits within blocks 20 and 21. Thermoelectric coolers cannot be directly embedded within blocks 20 and 21, since these elements consist of two plates: heat that is removed from one plate (the "cold" plate) is transferred to the other plate, which needs to be connected to a heat exchanger able to dissipate the heat. When using TECs, an embodiment such as the one shown for the top block in FIG. 9 is more appropriate.

FIG. 8 also illustrates a movable light source 70 that provides polarized light hv (the dash-dot line). Light hv from source 70 passes through sample 25 and is detected by a movable polarization detector 72. By moving the light and detector, in conjunction with one another, as illustrated by the double headed arrows, the light hv can be made to pass through different parallel planes of constant temperature (isothermal) planes. The stress distribution or profile within the sample is measured by measuring the changes in polarization state of the light traversing the sample. Any source of polarizable light (visible, infrared, ultraviolet) can be used. As an alternative to a movable, single-point measurement, the measurement can be accomplished by means of an extended light source (70e replacing 70, not illustrated) that illuminates the whole cross-section of sample 25, combined with an imaging polarimeter (72p replacing 72, not illustrated). An imaging polarimeter is a device able to measure the polarization state of the light over an extended field of view simultaneously, and in particular it can measure the polarization state of light passing through different isothermal planes.

Figure 9:
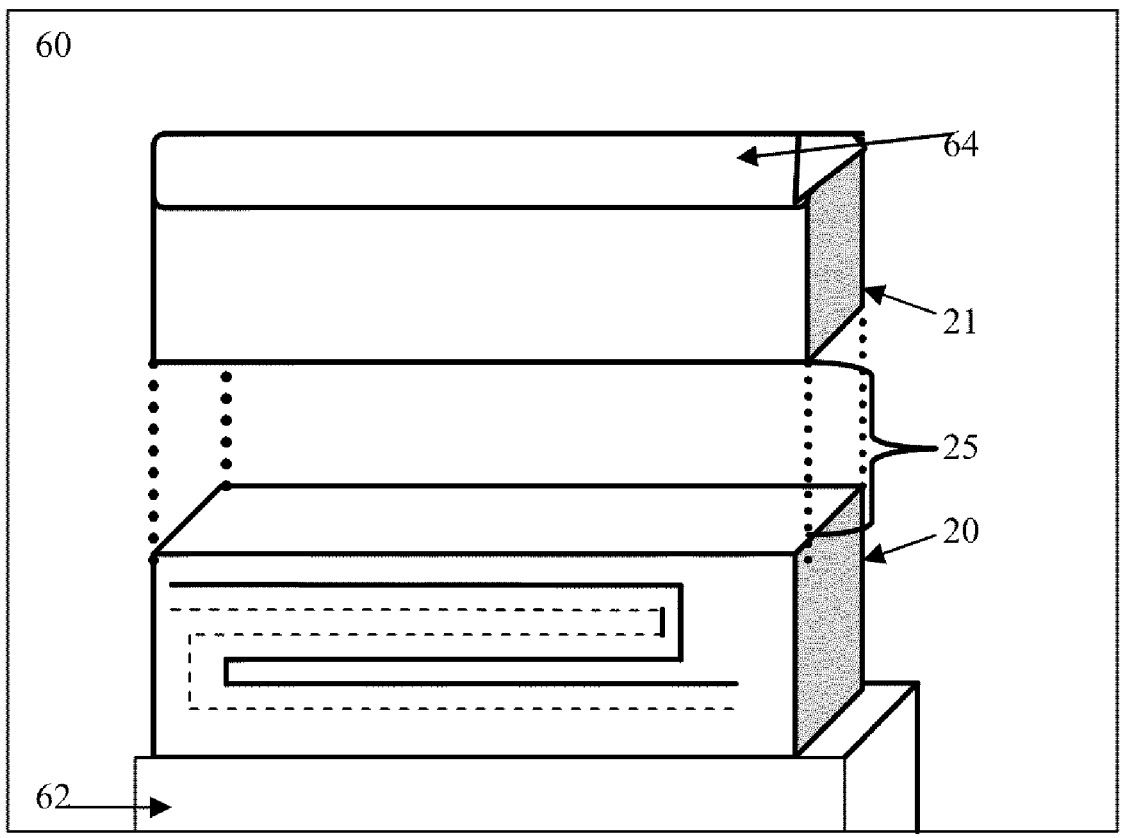
FIG. 9 is illustration of an embodiment using high thermal conductivity blocks in which one block has integrated heating and cooling elements and the other block has external heating and cooling elements, the elements being used to generate a vertical temperature gradient through a low thermal expansion glass, and further to the positions of the blocks and glass sample relative to one another within a vacuum chamber.

In FIG. 9 the heating and cooling elements are external to the top block 21 and are located within element 64. In another embodiment the bottom block 20 does not contain heating cooling elements, the heating/cooling elements being in an element similar to element 64 that is positioned between the bottom of block 20 and the top of stand 62. Sample 25 surfaces can be heated or cooled by separate control of the heating/cooling elements within the blocks to thereby generate a thermal gradient through the sample. In another embodiment the top of stand 62 is made of a high thermal conductivity material and the heating and cooling elements are located within the stand to thereby heat or cool the stand top and consequently block 20. The light source and detector for FIG. 9 are not illustrated, but are as discussed for FIG. 8, and are operated in the same manner.

In another embodiment the disclosure is directed to a method for determining the a zero crossover temperature of a material, for example, low expansion glasses, said method comprising:

providing a sample of a material having a selected length, width and height, and a first or top face and a second or bottom face, and a plurality of side faces, said material being transparent to light passing through the materials and having a zero crossover temperature in its expansivity versus temperature curve;

providing an apparatus having a top and a bottom block of a high thermal conductivity material, and elements for independently heating and/or cooling each of said blocks, a source of polarized light and a detector for measuring changes in the polarization of said light;

positioning said sample between said top and bottom blocks such that the top face of the sample is in thermal contact with the top block and bottom face or the sample is in contact with the bottom block;

independently heating or cooling the top and bottom faces to a selected temperature, wherein the selected top face temperature $T_t$ is different from the selected bottom face temperature $T_b$, and maintaining the selected temperature of the sample top and bottom faces for a time sufficient to establish a thermal gradient between the top and bottom faces of the sample;

measuring the stress distribution within the sample using a photo elastic technique consisting of measuring the changes in polarization state of polarized light traversing the sample in a direction parallel to the isothermal planes within the sample established by the thermal gradient to determine the horizontal sample plane having the highest tensile stress;

determining the temperature profile of the sample along the vertical axis; and determining Tzc from the temperature value of the plane having the maximum tensile stress. To determine the crossover temperature, some plane in the sample must be at the crossover temperature. Hence, $T_t>Tzc>T_b$, or $T_b>Tzc>T_t$. While the thickness of the part is generally smaller than the length or width, the thickness can be equal to or greater then either or both of the length or width of the part. The apparatus used is placed in a chamber selected from the group consisting of a room, an environmental chamber and a vacuum chamber.

In a further embodiment this disclosure is directed to a method for determining the temperature dependence of the expansivity of a material, for example, a low thermal expansion glass, said method comprising:

providing a sample of a material having a selected length, width and height, and opposing top and bottom faces, said material being transparent to light passing through the material and having a zero crossover temperature in its expansivity curve;

providing an apparatus having a top and a bottom block of a high thermal conductivity material, and elements for independently heating and/or cooling each of said blocks, a source of polarized light and a detector for measuring changes in the polarization of said light;

positioning said sample between said top and bottom blocks such that, as determined by the height, the top face of the sample is in thermal contact with the top block and bottom face is in contact with the bottom block;

independently heating or cooling the top and bottom faces to a selected temperature, wherein the selected top face temperature $T_t$ is different from the selected bottom face temperature $T_b$, and maintaining the selected temperature of the sample top and bottom faces for a time sufficient to establish a thermal gradient between the top and bottom faces;

measuring the stress distribution within the sample using a photo elastic technique consisting of measuring the changes in polarization state of polarizer light traversing the sample in a direction parallel to the isothermal planes within the sample established by the thermal gradient to determine the horizontal sample plane having the highest tensile stress;

determining the temperature profile of the sample along the vertical axis; and determining the expansivity slope from a mathematical fit of the vertical dependence of the measured stress distribution as a function of temperature after elasticity correction factors have been calculated. The apparatus used is placed in a chamber selected from the group consisting of a room, an environmental chamber and a vacuum chamber.

In another embodiment this disclosure is directed to an apparatus for determining the zero crossover temperature of low expansion glass and/or the temperature dependence of the thermal expansivity of low thermal expansion glass, the apparatus comprising:

a holder for holding the sample being evaluated, said holder comprising of a top block and a bottom block that can each be independently heated and/or cooled such when the top and bottom blocks are in contact with opposing faces of a sample in the holder, and the blocks are heated/cooled to different temperatures, a thermal gradient is established within the sample;

a source of polarized light; and a detector for detecting the polarization state of the light from the polarized light source, after it passes through the sample. The apparatus can be located in a chamber selected from the group consisting of a room, an environmental chamber and a vacuum chamber:

It will be apparent to those skilled in the art that various modifications and variations can be made to the present disclosure without departing from the spirit and scope of the disclosure. Thus, it is intended that the present disclosure cover the modifications and variations of this disclosure provided they come within the scope of the appended claims and their equivalents.

I claim:

1. A method for determining the CTE zero crossover temperature Tzc of a material, said method comprising:
    providing an apparatus having a top and a bottom block of a high thermal conductivity material, and elements for independently heating and/or cooling each of said blocks, a source of polarized light and a detector for measuring changes in the polarization of said light, and said apparatus being within a chamber;
    providing a sample of a material having a selected length, width and height, opposing top and bottom faces, and a plurality of side faces, said material being transparent to light passing through the material and said material having a zero crossover temperature in its expansivity versus temperature curve;
    positioning said sample between said top and bottom blocks such that the top face of the sample is in thermal contact with the top block and bottom face is in contact with the bottom block;
    independently heating or cooling the top and bottom faces of the sample to a selected temperature, wherein the selected top face temperature $T_t$ is different from the selected bottom face temperature $T_b$, and maintaining the selected temperature of the sample top and bottom faces for a time sufficient to establish a thermal gradient between the top and bottom faces;
    measuring the stress distribution within the sample using a photoelastic technique consisting of measuring the changes in polarization state of polarized light traversing the sample in a direction parallel to the isothermal planes within the sample established by the thermal gradient, to determine the horizontal sample plane having the highest tensile stress;
    measuring the temperature profile of the sample along the vertical axis; and
    determining Tzc from the temperature value of the plane having the maximum tensile stress;
    wherein said material is selected from the group consisting of glasses and glass-ceramics having a CTE zero crossover temperature Tzc.

2. The method according to claim 1, wherein the heating and cooling elements are selected from the group consisting of:
    (a) heating and cooling elements integrated into the blocks in thermal contact with the sample;
    (b) heating and cooling elements external to the blocks in thermal contact with the sample; and
    (c) heating and cooling elements are external to one of the blocks in contact with the sample and internal to the other of the blocks in contact with the sample.

3. The method according to claim 1, wherein the accuracy of the zero crossover temperature determination is ±1° C.

4. The method according to claim 1, wherein the accuracy of the zero crossover temperature determination is ±0.5° C.

5. The method according to claim 1, wherein the accuracy of the zero crossover temperature determination is ±0.2° C.

6. The method according to claim 1, wherein said chamber is a vacuum chamber and the chamber is evacuated to a pressure of less than $10^{-3}$ mm Hg before the faces of the samples are heated and/or cooled.

7. The method according to claim 1, wherein the material is a transparent glass or glass-ceramic having a CTE of <1 ppm/° C.

8. The method according to claim 1, wherein the light of polarized light source is selected from the group consisting of visible, infrared and ultraviolet light.

9. A method for determining the slope of the temperature dependence of the expansivity of a sample of low thermal expansion material, said method comprising:
    providing an apparatus having a top and a bottom block of a high thermal conductivity material, and elements for independently heating and/or cooling each of said blocks, a polarized light source and a detector for measuring changes in the polarization of said light, said apparatus being within a chamber;
    providing a sample of a low thermal expansion material having a selected length, width and height, the height being smaller than the length and width, opposing top and bottom faces and a plurality of side faces, said material being transparent to light passing through the material and said material having a zero crossover temperature in its expansivity versus temperature curve;
    positioning said sample between said top and bottom blocks such that the top face of the sample is in thermal contact with the top block and bottom face is in contact with the bottom block;
    independently heating or cooling the top and faces to a selected temperature, wherein the selected top face temperature $T_t$ is different from the selected bottom face temperature $T_b$, and maintaining the selected temperature of the sample top and bottom faces for a time sufficient to establish a thermal gradient between the top and bottom faces;
    measuring the stress distribution within the sample using a photoelastic technique consisting of measuring the changes in polarization state of a light beam traversing the sample in a direction parallel to the isothermal planes within the sample established by the thermal gradient;
    determining the temperature profile of the sample along the vertical axis; and
    determining the expansivity slope from a mathematical fit of the vertical dependence of the measured stress distribution as a function of temperature
    wherein said material is a glass or glass-ceramic having a CTE of <1 ppm/C.

10. The method according to claim 9, wherein said chamber is a vacuum chamber and the chamber is evacuated to a pressure of less than $10^{-3}$ mm Hg before the faces of the sample are heated and/or cooled.

11. The method according to claim 9, wherein the light of polarized light source is selected from the group consisting or visible, infrared and ultraviolet light.

12. An apparatus for determining the zero crossover temperature of low expansion materials, the apparatus comprising:
    a holder for holding a material sample being evaluated, said holder comprising of a top block and a bottom block that can each be independently heated and/or cooled such when the top and bottom blocks are in contact with opposing faces of a sample in the holder and are heated/cooled to different temperatures a thermal gradient is established within the sample;
    a source of polarized light; and
    a detector for detecting the polarization state of the light from the polarized light source, after it passes through the sample;

wherein the material sample tested is a transparent glass or glass-ceramic having a zero crossover temperature.

13. The apparatus according to claim 12, wherein the apparatus further comprises a vacuum chamber capable of reaching and maintaining a pressure of less than $10^{-3}$ mm Hg.

14. The apparatus according to claim 12, wherein the apparatus further comprises a vacuum chamber capable of reaching and maintaining a pressure of less than $10^{-4}$ mm Hg.

15. The apparatus according to claim 12, wherein the light of polarized light source is selected from the group consisting or visible, infrared and ultraviolet light.

16. A method for determining the zero crossover temperature of low expansion glasses, said method comprising:
   providing an apparatus having a top and a bottom block of a high thermal conductivity material, and elements for independently heating and/or cooling each of said blocks, a polarized light source and a detector for measuring changes in the polarization of said light, and placing said apparatus within a chamber;
   providing a sample of a low CTE glass having a selected length, width and height, opposing top and bottom faces, and a plurality of side faces;
   positioning said sample between said top and bottom blocks such that the top face of the sample is in thermal contact with the top block and bottom face is in contact with the bottom block;
   independently heating or cooling the top and bottom faces of the sample to a selected temperature, wherein the selected top face temperature $T_t$ is different from the selected bottom face temperature $T_b$, and maintaining the selected temperature of the sample top and bottom faces for a time sufficient to establish a thermal gradient between the top and bottom faces;
   measuring the stress distribution within the sample using a photoelastic technique consisting of measuring the changes in polarization state of a light beam traversing the sample in a direction parallel to the isothermal planes within the sample established by the thermal gradient, to determine the horizontal sample plane having the highest tensile stress;
   determining the temperature profile of the sample along the vertical axis; and
   determining the zero crossover temperature Tzc from the temperature value of the plane having the maximum tensile stress;
   wherein said low CTE glass has a CTE of <1 ppm/C.

17. The method according to claim 16, wherein the heating and cooling elements are selected from the group consisting of:
   (a) heating and cooling elements integrated into the blocks in thermal contact with the sample;
   (b) heating and cooling elements external to the blocks in thermal contact with the sample; and
   (c) heating and cooling elements are external to one of the blocks in contact with the sample and internal to the other of the blocks in contact with the sample.

18. The apparatus according to claim 16, wherein the apparatus further comprises a vacuum chamber capable of reaching and maintaining a pressure of less than $10^{-3}$ mm Hg.

* * * * *